(12) United States Patent
Eckhof et al.

(10) Patent No.: US 8,506,607 B2
(45) Date of Patent: Aug. 13, 2013

(54) ORTHOPEDIC SCREW FASTENER SYSTEM

(75) Inventors: Stephan Eckhof, Weilheim-Riethelm (DE); Josef Zrinski, Wurmlingen (DE); Zoran Reiter, Emmenigen-Liptingen (DE); Frank Altermann, Tuttlingen (DE); Rolf Maier, Liptingen (DE); Davor Zrinski, Welihelm-Rietheim (DE)

(73) Assignee: Zrinski AG, Wurmlingen (DE)

( * ) Notice: Subject to any disclaimer, the term of this patent is extended or adjusted under 35 U.S.C. 154(b) by 269 days.

(21) Appl. No.: 12/002,625

(22) Filed: Dec. 18, 2007

(65) Prior Publication Data

US 2009/0018588 A1 Jan. 15, 2009

(30) Foreign Application Priority Data

Dec. 19, 2006 (DE) .................... 20 2006 019 220 U (51) Int. Cl.
*A61B 17/80* (2006.01)
(52) U.S. Cl.
USPC ........................... 606/286; 606/291; 606/915
(58) Field of Classification Search
USPC ............. 606/280–299, 70–71; 411/160–165, 411/259, 260, 265, 276, 333
See application file for complete search history.

(56) References Cited

U.S. PATENT DOCUMENTS

| 1,322,863 | A | 11/1919 | Bach et al. |
|---|---|---|---|
| 1,691,676 | A | 11/1928 | Smith |
| 2,580,247 | A | 12/1951 | Secondi et al. |
| 3,741,205 | A | 6/1973 | Markolf et al. |
| 4,484,570 | A | 11/1984 | Sutter et al. |
| 4,488,543 | A | 12/1984 | Tornier |
| 4,711,234 | A | 12/1987 | Vives et al. |
| 4,755,184 | A | 7/1988 | Silverberg |
| 5,019,078 | A | 5/1991 | Perren et al. |
| 5,053,036 | A | 10/1991 | Perren et al. |
| 5,275,601 | A | 1/1994 | Gogolewski et al. |
| 5,601,553 | A | 2/1997 | Trebing et al. |
| 5,766,175 | A | 6/1998 | Martinotti |
| 5,954,722 | A | 9/1999 | Bono |
| 5,961,524 | A | 10/1999 | Crombie |

(Continued)

FOREIGN PATENT DOCUMENTS

| CA | 2 367 088 | 9/2000 |
|---|---|---|
| DE | 860 329 | 12/1952 |

(Continued)

OTHER PUBLICATIONS

US 7,201,752 4/2007, Huebner et al. (withdrawn).

(Continued)

*Primary Examiner* — Michael T Schaper
(74) *Attorney, Agent, or Firm* — Collard & Roe, P.C.

(57) ABSTRACT

An orthopedic screw fastener system, includes at least one screw, consisting in each case of a screw head and of a screw shank, the screw head being provided with a thread, and at least one plate with a thickness, provided with at least one through-bore which is able to receive a screw. The plate has a through-opening, formed by at least two through-bores, each through-bore being defined by a midpoint and by a radius, and the through-bores are offset relative to each other and intersect each other in such a way that intersection lines and/or intersection surfaces form, which extend into the depth of the through-opening.

8 Claims, 10 Drawing Sheets

(56) References Cited

U.S. PATENT DOCUMENTS

| | | | |
|---|---|---|---|
| 6,080,159 | A | 6/2000 | Vichard |
| 6,160,487 | A | 12/2000 | DeLuca |
| 6,179,839 | B1 | 1/2001 | Weiss et al. |
| 6,206,881 | B1 | 3/2001 | Frigg et al. |
| 6,258,089 | B1 | 7/2001 | Campbell et al. |
| 6,322,562 | B1 | 11/2001 | Wolter |
| 6,626,907 | B2 | 9/2003 | Campbell et al. |
| 6,656,181 | B2 | 12/2003 | Dixon et al. |
| 6,786,909 | B1 | 9/2004 | Dransfeld et al. |
| 6,890,335 | B2 | 5/2005 | Grabowski et al. |
| 6,908,467 | B2 | 6/2005 | Ip et al. |
| 6,944,677 | B1 | 9/2005 | Zhao |
| 6,955,677 | B2 | 10/2005 | Dahners |
| 6,974,461 | B1 | 12/2005 | Wolter |
| 7,276,070 | B2 | 10/2007 | Mueckter |
| 7,621,938 | B2 | 11/2009 | Molz, IV |
| 2003/0014054 | A1 | 1/2003 | Huebner |
| 2004/0102775 | A1 | 5/2004 | Huebner |
| 2004/0102776 | A1 | 5/2004 | Huebner |
| 2004/0102777 | A1 | 5/2004 | Huebner |
| 2004/0102778 | A1 | 5/2004 | Huebner et al. |
| 2004/0102788 | A1 | 5/2004 | Huebner et al. |
| 2004/0127901 | A1 | 7/2004 | Huebner et al. |
| 2004/0181221 | A1 | 9/2004 | Huebner et al. |
| 2004/0181228 | A1* | 9/2004 | Wagner et al. ............... 606/69 |
| 2005/0085818 | A1 | 4/2005 | Huebner |
| 2005/0101961 | A1 | 5/2005 | Huebner et al. |
| 2005/0165400 | A1 | 7/2005 | Fernandez |
| 2005/0234472 | A1 | 10/2005 | Huebner |
| 2005/0240187 | A1 | 10/2005 | Huebner et al. |
| 2006/0009771 | A1* | 1/2006 | Orbay et al. ............... 606/69 |
| 2006/0106390 | A1 | 5/2006 | Jensen et al. |
| 2006/0106393 | A1 | 5/2006 | Huebner et al. |
| 2006/0116678 | A1 | 6/2006 | Impellizzeri |
| 2006/0149249 | A1 | 7/2006 | Mathoulin et al. |
| 2006/0200134 | A1 | 9/2006 | Freid et al. |
| 2006/0229622 | A1 | 10/2006 | Huebner et al. |
| 2006/0235400 | A1* | 10/2006 | Schneider ............... 606/69 |
| 2006/0264946 | A1* | 11/2006 | Young ............... 606/69 |
| 2007/0055249 | A1 | 3/2007 | Jensen et al. |
| 2007/0055251 | A1 | 3/2007 | Huebner et al. |
| 2007/0123878 | A1 | 5/2007 | Shaver et al. |
| 2007/0162018 | A1 | 7/2007 | Jensen et al. |
| 2007/0173840 | A1 | 7/2007 | Huebner |
| 2007/0276405 | A1 | 11/2007 | Huebner et al. |
| 2008/0082175 | A1 | 4/2008 | Holovacs et al. |
| 2008/0140130 | A1 | 6/2008 | Chan et al. |
| 2008/0161861 | A1 | 7/2008 | Huebner |
| 2009/0069851 | A1 | 3/2009 | Gillard et al. |
| 2009/0076554 | A1 | 3/2009 | Huebner et al. |
| 2009/0143824 | A1 | 6/2009 | Austin et al. |
| 2010/0030276 | A1 | 2/2010 | Huebner et al. |
| 2010/0030277 | A1 | 2/2010 | Haidukewych et al. |
| 2010/0228299 | A1 | 9/2010 | Zrinski et al. |
| 2010/0324602 | A1 | 12/2010 | Huebner et al. |
| 2011/0022049 | A1 | 1/2011 | Huebner et al. |
| 2011/0137351 | A1 | 6/2011 | Huebner et al. |
| 2011/0196491 | A1 | 8/2011 | Huebner |

FOREIGN PATENT DOCUMENTS

| | | |
|---|---|---|
| DE | 1 834 650 | 7/1961 |
| DE | 76 25 614 | 1/1977 |
| DE | 2938202 | 2/1981 |
| DE | 33 01 298 | 2/1984 |
| DE | 86 10 858 | 6/1986 |
| DE | 86 28 766 | 12/1986 |
| DE | 40 04941 | 8/1990 |
| DE | 37 89 876 | 11/1994 |
| DE | 43 41 980 | 6/1995 |
| DE | 43 43 117 | 6/1995 |
| DE | 692 16 009 | 4/1997 |
| DE | 196 29 011 | 1/1998 |
| DE | 199 62 317 | 3/2001 |
| DE | 199 51 760 | 6/2001 |
| DE | 203 09 361 | 10/2003 |
| DE | 203 17 651 | 3/2004 |
| DE | 20 2004 015 912 | 12/2004 |
| DE | 203 21 245 | 6/2006 |
| DE | 10 2005 004 841 | 7/2006 |
| DE | 20 2008 005 076 | 10/2008 |
| DE | 202008005076 | 10/2008 |
| EP | 0 016 338 | 10/1980 |
| EP | 0 369 266 | 5/1990 |
| EP | 0 468 192 | 1/1992 |
| EP | 0 530 585 | 3/1993 |
| EP | 0 848 600 | 6/1998 |
| EP | 1 143 867 | 10/2001 |
| EP | 1 158 916 | 12/2001 |
| EP | 1 211 994 | 6/2002 |
| EP | 1 649 819 | 4/2006 |
| EP | 1935359 | 6/2008 |
| FR | 742 618 | 3/1933 |
| FR | 742618 | 3/1933 |
| FR | 2848413 | 6/2004 |
| WO | WO 89/04150 | 5/1989 |
| WO | WO 97/09000 | 3/1997 |
| WO | WO 00/36984 | 6/2000 |
| WO | WO 00/53111 | 9/2000 |
| WO | WO 00/66012 | 11/2000 |
| WO | WO0119264 | 3/2001 |
| WO | WO 02/098276 | 12/2002 |
| WO | WO 2004/084701 | 10/2004 |
| WO | WO 2005018472 A1 * | 3/2005 |
| WO | WO 2007/014192 | 2/2007 |
| WO | WO 2008/075153 | 6/2008 |
| WO | WO 2008/075160 | 6/2008 |

OTHER PUBLICATIONS

International Search Report dated Jun. 6, 2008 for WO 2008/075153 (Application No. PCT/IB2007/003838) which was filed on Dec. 10, 2007. 8 pages.

European Search Report for EP 07122696 on Apr. 25, 2008 (European Application Corresponding to Priority Application DE 202006019220.

* cited by examiner

ORTHOPEDIC SCREW FASTENER SYSTEM

CROSS-REFERENCES TO RELATED APPLICATIONS

This application claims convention priority under 35 U.S.C. §119 from German Utility model DE 20 2006 019 220.4 filed on Dec. 19, 2006, from European Application EP 07122696.3 filed Dec. 10, 2007, and from International Application PCT/IB2007/003838 filed Dec. 10, 2007.

BACKGROUND TO THE INVENTION

1. Field of the Invention

The present invention relates to a screw fastener system, consisting of at least one screw and of at least one plate with at least one through-bore. The screw itself consists of a screw head and of a screw shank, at least the screw head being provided with a thread. The screw can be inserted multiaxially into the through-bore. This means that the screw can be inserted, not perpendicular to the plate, but obliquely with respect to the plate, and can be locked on the plate. A force-fit connection, or a force-fit and form-fit connection, is obtained between the screw and the plate.

2. Definitions

Through-Bore

Through-bore defines bores that extend from the top of a plate to the underside of the plate. It can be cylindrical or conical in shape. Generally, it can be produced using a drill or a milling cutter.

Through-Opening

Through-opening defines openings that are suitable for receiving a screw with screw shank and screw head. In the through-opening, the screw head establishes the force-fit and form-fit connection with the rest of the plate. The through-opening is generally formed initially by two or more through-bores that are arranged relative to one another in such a way that they intersect. To produce a through-opening, a central bore is first made, and further through-bores are formed from this at regular intervals, such that a structure is obtained which, in plan view, looks like a clover or flower or leaf.

Intersection Line

If several through-bores intersect, then intersection lines form in the area of the through-openings and extend through the thickness of the plate. The intersection lines thus extend into the depth of the through-opening. They are preferably configured such that they extend in the direction of the longitudinal extent of the through-bore. The intersection lines are elements that interact with the screw head to bring about a force-fit and form-fit connection through plastic deformation.

Intersection Surface

The intersection lines defined above then become intersection surfaces, if the through-bore and/or the central bore are conical in shape. The intersection surfaces are elements that interact with the screw head to bring about a force-fit and form-fit connection through plastic deformation. For simplicity, only intersection lines will be discussed below. Unless otherwise stated, however, this is also understood to cover the combination of intersection lines and intersection surfaces or only the intersection surfaces.

3. The Prior Art

Screws and plates, in particular bone plates, of the aforementioned type generally form a fixation system and are mainly used to mechanically stabilize bone fractures. This fixation system consists of a plate, which is provided with at least one through-bore, but generally with several through-bores, said through-bores being designed in each case to receive a screw. The screw itself consists of a screw head and of a screw shank and, on the screw shank, has a thread that is able to be screwed into a bone. The screw head itself also has a thread which, in the assembled state of the fixation system, interacts with the plate in the respective through-bore.

Orthopedic fixation devices can be used both outside and also inside the body. They consist of a plate-shaped structure, which extends over a fracture, for example. Securing means are also provided, which are designed, for example, as screws, bolts, nails or pins. For example, so-called bone plates can be secured on a bone by means of bone screws, by the latter being inserted through through-bores and being screwed into the bone. To ensure that these screws do not come loose, particularly under the effect of forces, a great many mechanisms are known from the prior art which avoid loosening of the screw and, consequently, loosening of the plate-shaped structure. Solutions are also known that permit, between the plate and the screw, a force-fit connection in which the screw is not oriented perpendicular to the plate. An oblique position of such a screw is often desired if, for example on account of the bone structure, it is not possible for the screw to be screwed perpendicular to the plate.

Thus, for example, so-called expansion-head screws are known from U.S. Pat. No. 4,484,570 (SYNTHES LTD (US)) Nov. 27, 1984. A head screw that has been screwed into a plate is spread open by an additional screw element in such a way that, by screwing in the additional screw, a wedging effect takes place within the plate, such that the screw is fixed on the plate.

Another embodiment from the prior art, as set out for example in U.S. Pat. No. 5,954,722 (DEPUY ACROMED INC (US)) Sep. 21, 1999, comprises a plate into which a screw can be screwed multiaxially. The multiaxial aspect has, among other things, the advantage that the screwing-in directions are no longer defined by the plate itself. In this way, depending on the nature of the material, it is no longer essential for a screw to be screwed into a bone perpendicular to the longitudinal extent of the plate. For this purpose, the through-bores are additionally provided with a spherical element, which is mounted so as to be at least partially rotatable within the through-bore. This spherical element is arranged captive within the through-bore and interacts with the screw head of the screw that is to be screwed in. The spherical element orients itself depending on the position and thus establishes a force-fit and form-fit connection with the screw head and the plate.

Another multiaxial design of a plate, which interacts with a specially designed screw, is set out in US 20050165400 A (FERNANDEZ ALBERTO A, UY) Jan. 26, 2004. The orthopedic fixation system comprises a plate, which likewise has one or more through-bores. A screw is also provided, which consists of a screw head and of a screw shank. The screw head is specially designed and has a thread that interacts with threads provided at least partially in the through-bores.

To allow a screw to be screwed in obliquely (and thus not perpendicular) to the longitudinal extent of the plate, provision is made for the through-bore to be specially designed. The through-bores have an hourglass-shaped cross section. This means that, seen in the screwing-in direction, the diameter of the through-bore narrows from an initially wide diameter until a defined plane is reached. Starting from this plane, the diameter of the through-bore widens out again.

The through-bore formed in this way has a thread, which interacts with the thread of the screw head. The thread is specially designed and constitutes a so-called cutting thread. This means that, when the screw head is being screwed in, a mechanical cutting process takes place between said thread and the screw head. To strengthen this cutting process and thereby achieve a wedging of the screw head within the through-bore, such that undesired loosening of plate and screw at a later point is no longer possible, cutting elements preferably made of another material are provided within the through-bore. These cutting elements are let into the circumference of the through-bore and bring about a deformation when the screw is screwed into the through-bore. By means of the spherical shape of the screw head, it is possible to choose a large number of angle degrees that deviate from the line perpendicular to the longitudinal extent of the plate.

DE 202004015912U (AESCULAP AG) Dec. 9, 2004 also discloses a fixation system that consists principally of a plate and of a bone screw. The bone screw itself has a shank, which defines a longitudinal axis, and a screw head, which can be brought into engagement with a bone screw seat. A securing element for securing the connection of bone screw and bone plate is additionally provided, the bone screw being able to be brought from a position of engagement, in which the bone screw is held on the bone plate, to a release position.

The through-bores within the bone plate are preferably oval in shape, thereby permitting multiaxial engagement of the bone screw. On their walls, they have threads that can be brought into engagement with the thread of the bone screw or screw head. Securing of the bone screw is achieved by wedging the bone screw to the bone plate. The through-bores are produced by milling an oval through-opening, which has walls formed perpendicular to the longitudinal extent of the bone plate. The walls additionally have thread turns. The production is therefore expensive and complex. The bone screw itself has to be specially designed and have the special securing mechanism available.

WO 2004/084701 A (SWISS ORTHOPEDIC SOLUTIONS SA (CH); YOUNG ROBERT ALLAN (US)) Oct. 7, 2004 discloses a bone plate having a longitudinal extent. The bone plate itself has several through-openings, formed in each case by two through-bores offset relative to each other. The through-bores are arranged in such a way that their midpoint is arranged on the center axis of the respective bone plate and arranged at a defined distance from one another. The two through-bores intersect each other in such a way that, in plan view, a configuration in the shape of an eight is obtained. This means that a narrowing is provided between the two through-bores that form the through-opening. In the lower area, that is to say the area facing toward the bone, both through-bores have thread turns that are different than each other. On the side facing away from the bone, that is to say the top, the area of aperture of the through-bore, and thus also of the through-opening, is much greater than in the lower area.

In particular illustrative embodiments, the thread turns provided in the lower area of the bone plate are arranged at an angle to one another or obliquely.

As in the other prior art, it is necessary to produce the bone plate in different work cycles. In particular, in the lower area of the bone plate, that is to say the area facing toward the bone, it proves difficult to arrange different thread turns that can then interact with the head of the bone screw, which likewise has a thread. A free multiaxial arrangement of the bone screw is therefore not possible, since, when being screwed in, it inevitably interacts with the thread and thus also assumes the predetermined direction.

DE 20321245U (SYNTHES GMBH (CH)) Jun. 14, 2006 also discloses a bone plate with an underside facing toward the bone and with a top, and with several through-bores, which connect the underside to the top and each have a central hole axis, an inner jacket surface and a thread turn. In a particular illustrative embodiment, the through-opening is formed by a central through-bore with, arranged on the circumference of the through-bore, through-bores arranged at an angle distance of in each case 90 degrees from one another.

This permits a multiaxial arrangement of the respective bone screws, the head thereof each being inserted into the respective through-bore. The respective through-bores likewise comprise thread turns, as has already been described above.

For this reason, the production is also very complex, and the multiaxial direction of the respective bone screw cannot be freely chosen, on account of the corresponding specifications of the through-bores.

Moreover, there is no possibility of securing the respective bone screw, such that undesired loosening is possible at any time, as a result of which there is a danger of the function of the respective bone plate being completely lost.

SUMMARY OF THE INVENTION

Object of the Invention

The object of the invention is to make available a plate or a simple screw fastener system, consisting of screw and plate, for attachment to bone, with which a screw can be screwed in multiaxially with respect to the plate or to the surface of the bone, and the screw can be secured against undesired loosening.

Solution

The underlying concept of the solution is that the plate has at least two through-bores, each through-bore being defined by a midpoint and by a radius. The through-bores themselves are offset relative to each other and intersect each other in such a way that intersection lines are obtained in the direction of the thickness of the plate, these intersection lines interacting with the thread of the screw head. A plastic deformation thus takes place between the screw head and/or the intersection lines, and this leads to a force-fit and form-fit connection between plate and screw.

Advantages of the Invention

One of the main advantages of the invention is that, despite the possibility of multiaxial engagement of the screws, the plate does not need to have a thread. The creation of the through-bore in the plate in itself generates projections or intersection lines, which permit in particular a multi-axial screwing-in of the screw into the plate. The resulting plastic deformation also has the effect that loosening of the screw from the plate is possible only with application of considerable force. Unwanted loosening is not possible.

Advantageously, at least three through-bores are provided, which are arranged relative to one another in such a way that all three through-bores intersect. This means that the first through-bore intersects the second through-bore and the third through-bore, the second through-bore intersects the first and third through-bores, and the third through-bore intersects the first and second through-bores. This results in three intersection lines, which extend into the thickness and thus into the depth of the plate. In the middle, a through-opening is centrally obtained whose radius is defined by the distance of an intersection line from the midpoint of the through-opening.

A preferred embodiment provides for a symmetrical configuration of the through-bores starting from a central bore. For this purpose, the through-bores provided in the plate are arranged in such a way that their respective midpoints are arranged on an arc of a circle, starting from the midpoint of the central bore. This produces a flower-shaped, leaf-shaped or cloverleaf-shaped arrangement of the through-bores around the midpoint of the central bore. If several through-bores are used, several projections or intersection lines are also obtained, which can then once again interact with the screw head of the screw. The number of through-bores is not limited. The number of through-bores for creating a through-opening is proportional to the intersection lines.

An important advantage is seen in the fact that no defined top face and underside of the bone plate is provided. This means that the plate can be used functionally correctly, irrespective of its position.

All the aforementioned bores of a particular embodiment are cylindrical. This means that the diameter of the through-bores and thus also of the through-opening remains constant over the thickness of the plate.

The intersection lines or intersection surfaces obtained through the cutting of the respective through-bores are configured in such a way that, in a plan view of the plate, they narrow toward the respective center of the through-opening. They have a cross section which is configured in such a way that, starting from the walls of the through-bore, it narrows in the direction of the center of the through-opening. In an illustrative embodiment in which the through-bores are each applied perpendicular to the plate, the cross section, through the depth of the plate, of the respective intersection line or intersection surface is constant. This means that, already when the screw is mounted on the plate according to the invention with the corresponding inventive design of the through-opening, it comes into engagement already with the first turn, so as to permit better screwing in, provision can also be made that the respective through-bore and thus also the whole through-opening is countersunk. In this way, the screw can first be inserted into the through-opening, can be suitably placed there and, only in a further step, can then be brought into engagement with the respective intersection line or intersection surface.

If the through-bores are oblique, that is to say not perpendicular to the longitudinal extent of the plate, this also results in oblique intersection lines or intersection surfaces extending into the depth of the plate. If these are formed at different angles, conical formations are also obtained.

At their free ends, the intersection lines then each have a very small thickness. In this way, it is possible for the thread of the screw head to cut in easily in these areas, since the resistance is slight, on account of the small thickness. The V-shaped configuration of the areas of the intersection lines, as seen in plan view, are such that the cross section becomes thicker the greater the distance from the free end of the intersection line. This is particularly so when the screw heads are of conical shape, a greater cross section being penetrated by the thread of the screw as the screwing-in of the screw increases. A strong plastic deformation thus takes place.

In a preferred embodiment, after production of a central bore, the through-bores are not formed cylindrically in the direction of thickness of the plate, but conically. The conicity is such that the through-bore narrows from the screwing-in direction toward the bone. This is advantageously achieved through using a conical milling cutter. Its axis of symmetry is preferably parallel to the axis of the central bore and also perpendicular to the plate. The midpoints of the through-bores are chosen such that their radius, which is preferably the same in all the through-bores, intersects the diameter of the central bore, resulting in a through-opening which is larger than the diameter of the central bore and, on its outer wall, has a large number of conical walls. The individual walls are conically shaped and narrow in the screwing-in direction. Thus, in the screwing-in direction, intersection lines are first obtained (since the diameter of the individual through-bores is large), whereas with increasing depth (in the screwing-in direction) the diameter of the through-bores decreases, because of the provided conicity, and intersection surfaces are therefore obtained between the individual through-bores.

It was found that the number of through-bores is almost proportional to the screwing-in force of the screw. This means that, with a larger number of through-bores (for example 15), the screwing-in force is smaller compared to a smaller number of through-bores (for example 5).

Provision is made in principle for more force to be applied as the depth of insertion of the screw into the plate increases. The reason for this is that first an interaction takes place, preferably a deformation with the intersection lines. The line or volume provided in engagement with the screw is small. When the intersection line merges into an intersection surface, the volume to be deformed by the screw becomes greater, and, consequently, more force has to be applied. However, this also has the effect of achieving a secure, non-releasable connection between the plate and the screw.

In a preferred development, the central bore is first produced with a conical cross section. A defined conicity is chosen. The through-bores, which follow in the shape of a cloverleaf in relation to this central bore, also have a conicity, but a different one than the central bore. In this way, intersection surfaces, not intersection lines, are obtained in the remote screwing-in area within the through-bore.

Screw head and screw shank preferably have the same diameter. This affords the advantage that the screw is easy to produce.

Alternatively, provision can also be made for the screw head to be made cylindrical and to have a different thread turn than the rest of the shank.

In another alternative, the screw head can be made conical and thus adapts to the shape of the through-bore.

The screw shank itself can also be made conical, in order thereby to reduce the force applied, particularly when screwing the screw into the bone.

In another alternative embodiment, the screw head is made at least partially spherical. In this way, it is possible to achieve a greater angle, deviating from the line perpendicular to the plate, by the screw still being able to be screwed obliquely (multiaxially) in the plate.

Thus, a system has been proposed consisting exclusively of two structural parts. It is not necessary to use additional expanding elements or shim elements or other materials. Screw and plate can preferably be made from the same material. To further improve the plastic deformation, particularly in the area of the projections, provision can be made for the plate to be produced from a softer material than the screw itself.

One of the main advantages of the system lies in the fact that the plate itself can be produced with minimal outlay. The simplest form is to provide three through-bores, which are to be configured in a defined arrangement to one another, such that a through-opening is obtained into which the screw can be inserted.

In the preferred embodiment, a central bore is to be provided in the plate, which is cut from through-bores, said through-bores being produced with a conical mill, which narrows in the screwing-in depth. The number of through-bores should be greater than 5. A preferred number is 15.

In another advantageous embodiment, the intersection lines and/or intersection surfaces are hardened and thus provide a harder property compared to the rest of the material of the plate. Such hardening can be carried out by laser, for example.

Other advantageous embodiments will become clear from the attached drawings, from the description, and also from the claims.

ILLUSTRATIVE EMBODIMENT

DETAILED DESCRIPTION OF A PREFERRED EMBODIMENT

Figure 1:
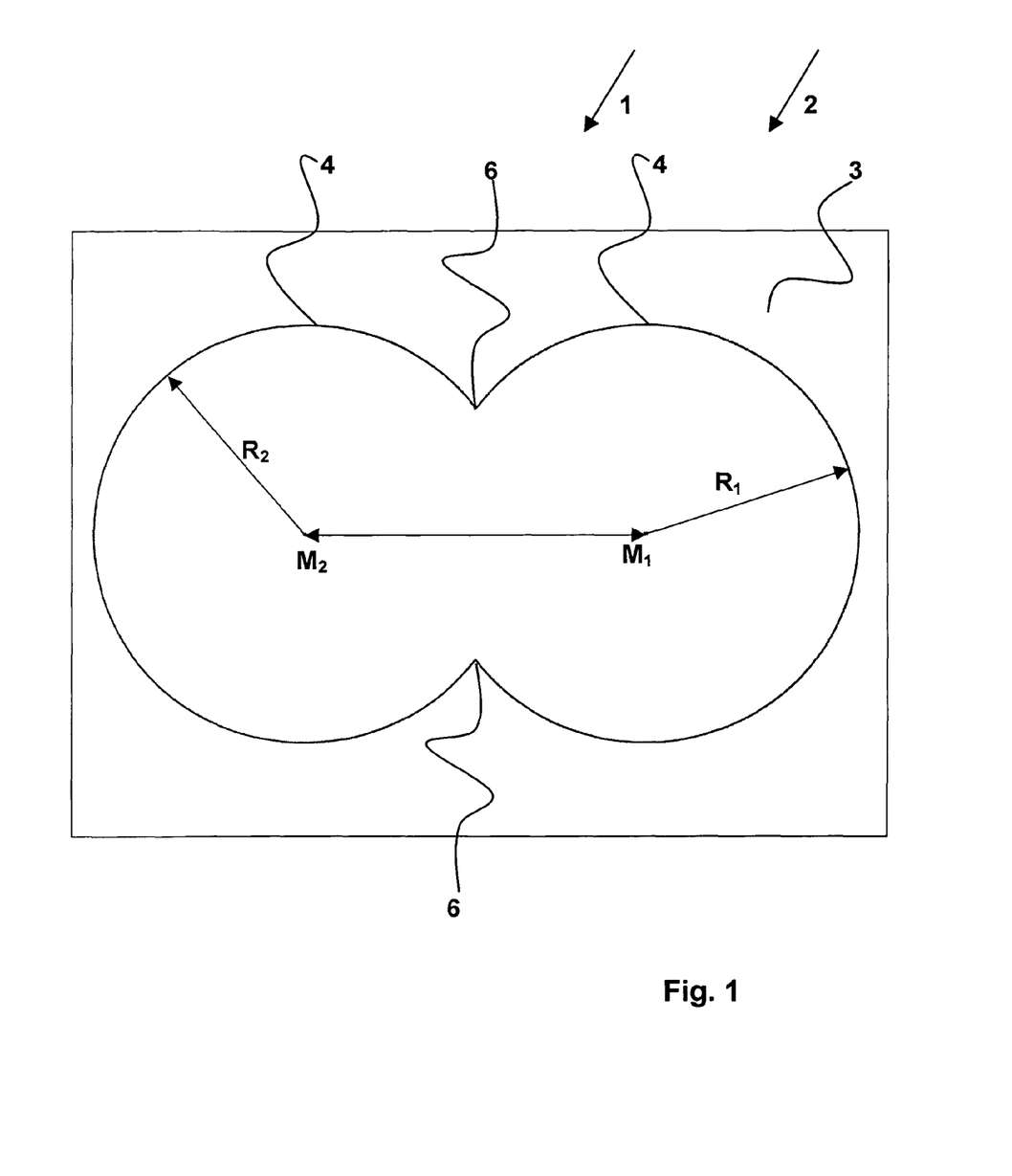
FIG. 1 shows a first illustrative embodiment of a schematic representation of a through-opening of a plate as part of the screw fastener system according to the invention.
Figure 2:
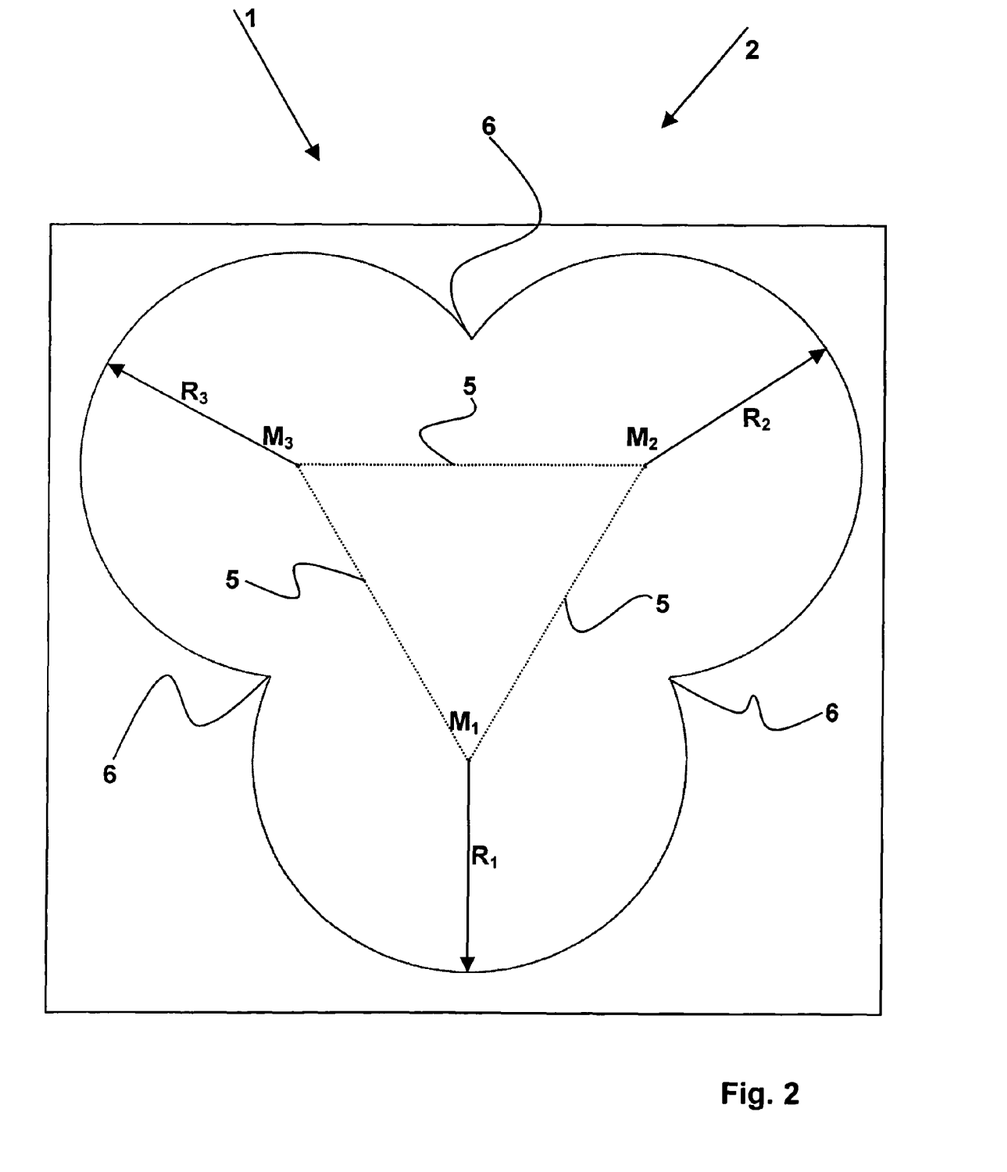
FIG. 2 shows a second illustrative embodiment of a schematic representation of a through-opening of a plate as part of the screw fastener system according to the invention.
Figure 3:
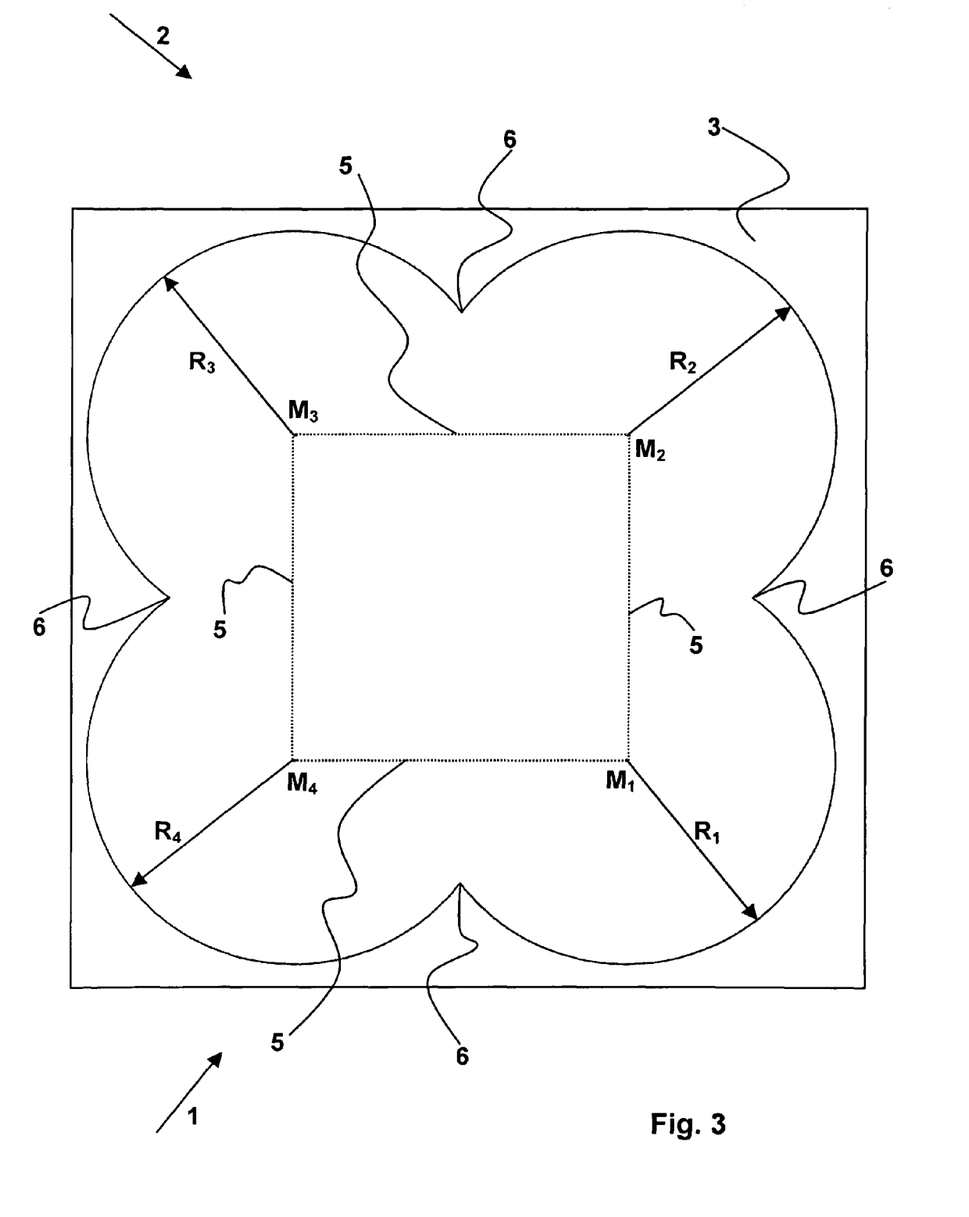
FIG. 3 shows a third illustrative embodiment of a schematic representation of a plate as part of the screw fastener system according to the invention.

FIGS. 1 to 3 show a selection of possible through-openings 1 for an orthopedic screw fastener system 2. To produce such a through-opening 1 according to the invention, arranged on a plate 3, at least two through-bores 4 are generated. Each through-bore $4_x$ is defined by a radius $R_x$ and a midpoint $M_x$.

According to a first illustrative embodiment, as shown in FIG. 1, the through-opening 1 consists of two through-bores 4 whose two midpoints $M_1$, $M_2$ are arranged at a distance 5 from each other. The distance 5 is to be chosen such that the two radii $R_1$, $R_2$ of the through-bores 4 intersect. This results in intersection lines 6, which extend into the depth (thickness) of the plate 3. The intersection lines 6 are configured in such a way that they are designed tapering toward the free space of the through-opening 1 and have a thicker wall thickness as their distance from the latter increases. In this way, it is possible that the free ends thus formed can be plastically deformed by screwing-in of a screw.

According to another illustrative embodiment, as shown in FIG. 2, the through-opening 1 consists of three through-bores 4 whose midpoints $M_1$, $M_2$, $M_3$ are each arranged at a distance 5 from one another. The respective distance 5 is to be chosen such that the three radii $R_1$, $R_2$, $R_3$ of the through-bores 4 intersect. This results in intersection lines 6, which extend into the depth (thickness) of the plate 3.

According to another illustrative embodiment, as shown in FIG. 3, the through-opening 1 consists of four through-bores 4 whose midpoints $M_1$, $M_2$, $M_3$, $M_4$ are each arranged at a distance 5 from one another. The respective distance 5 is to be chosen such that the four radii $R_1$, $R_2$, $R_3$, $R_4$ of the through-bores 4 intersect. This results in intersection lines 6, which extend into the depth (thickness) of the plate 3.

Figure 4:
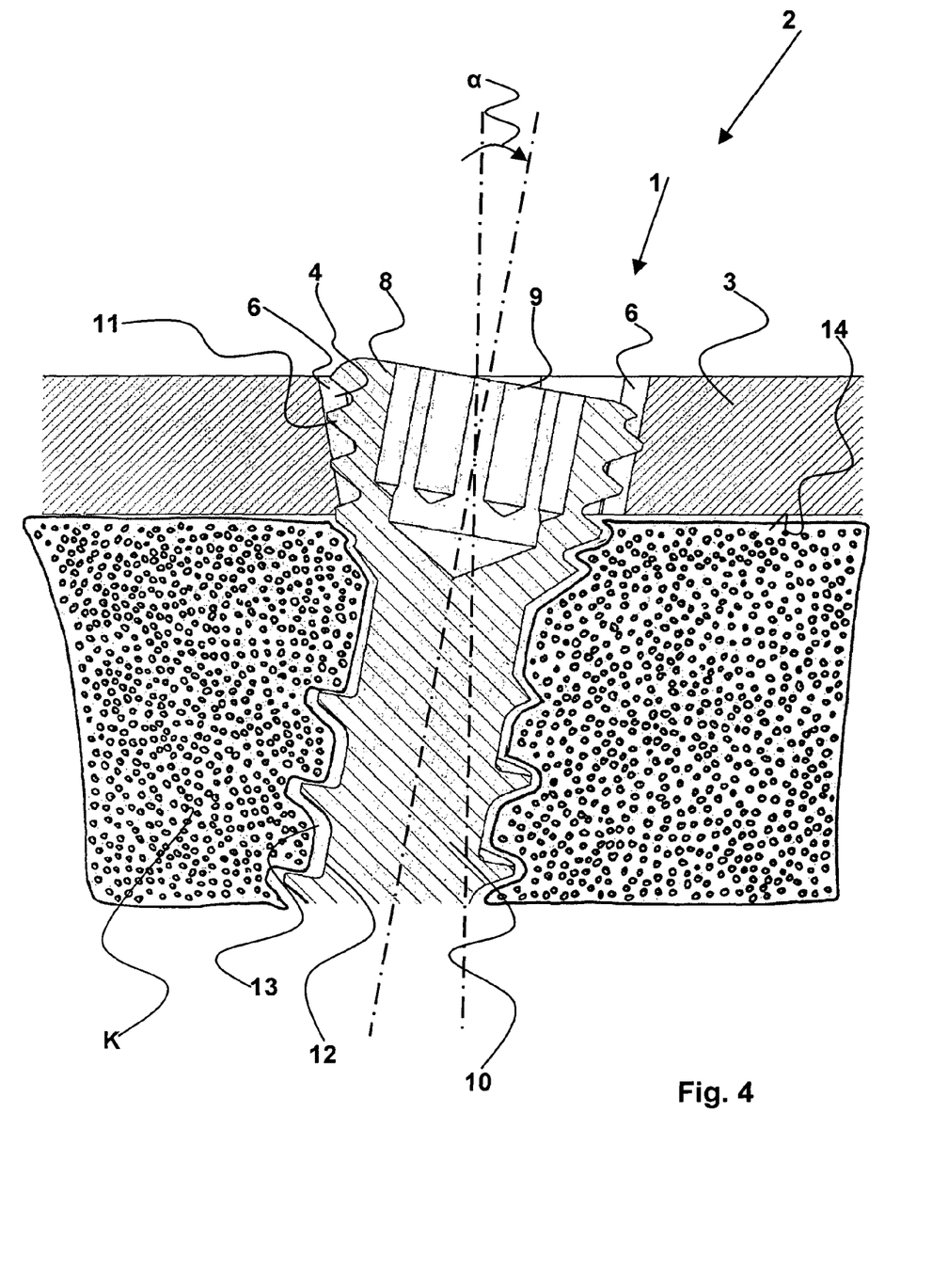
FIG. 4 shows a schematic representation of the orthopedic screw fastener system in cross section, the screw having already been screwed into the plate.

FIGS. 4, 5A, 5B and 6 show the orthopedic screw fastener system 2. It consists of a screw 8 and of the plate 3, as is shown for example in FIGS. 1 to 3. The plate 3 is used for fixing a fracture, for example. The screw 8 itself is screwed into a bone K. The plate 3 lies with its underside 14 on the outer face of the bone K (FIG. 4). The through-opening 1, as is shown by way of example in FIGS. 1-3, is used to receive the screw 8, which consists of a screw head 9 and of a screw shank 10. The screw head 9 and the screw shank 10 each have a thread. The thread 11 of the screw head 8 interacts with the intersection lines 6. The thread 12 of the screw shank 10 interacts with the bone K. In the bone K itself, a bore 13 is preferably already provided whose clear width is smaller than the diameter of the screw shank 10. By virtue of the fact that the clear width of the through-opening 1 is greater than that of the diameter of the screw head 9, it is possible, as is also shown in FIG. 4, to arrange the screw 8 not perpendicular to the plate 3, but inclined at any desired angle.

Figure 5A:
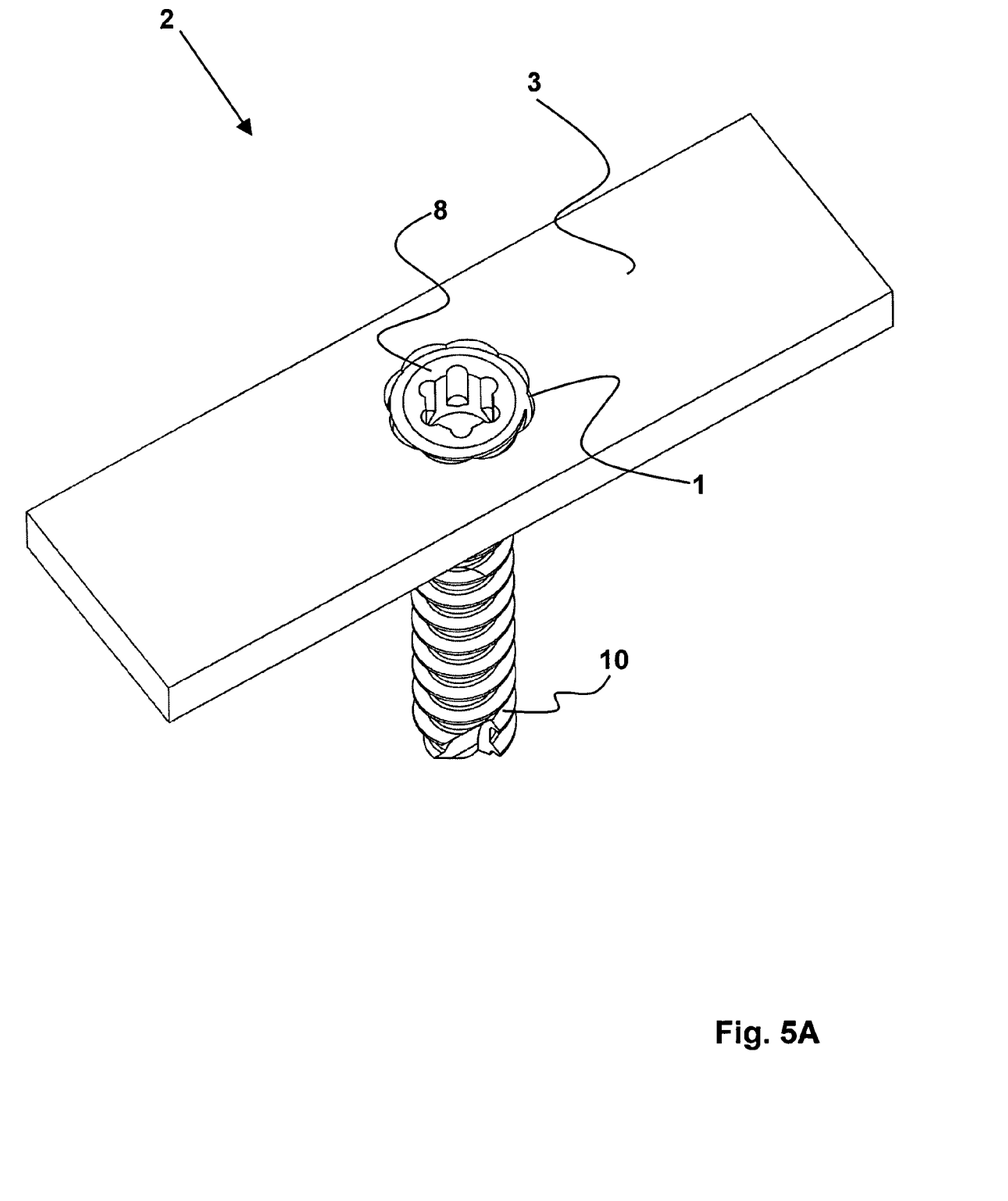
FIG. 5A shows a perspective view of the screw fastener system according to FIG. 4.
Figure 5B:
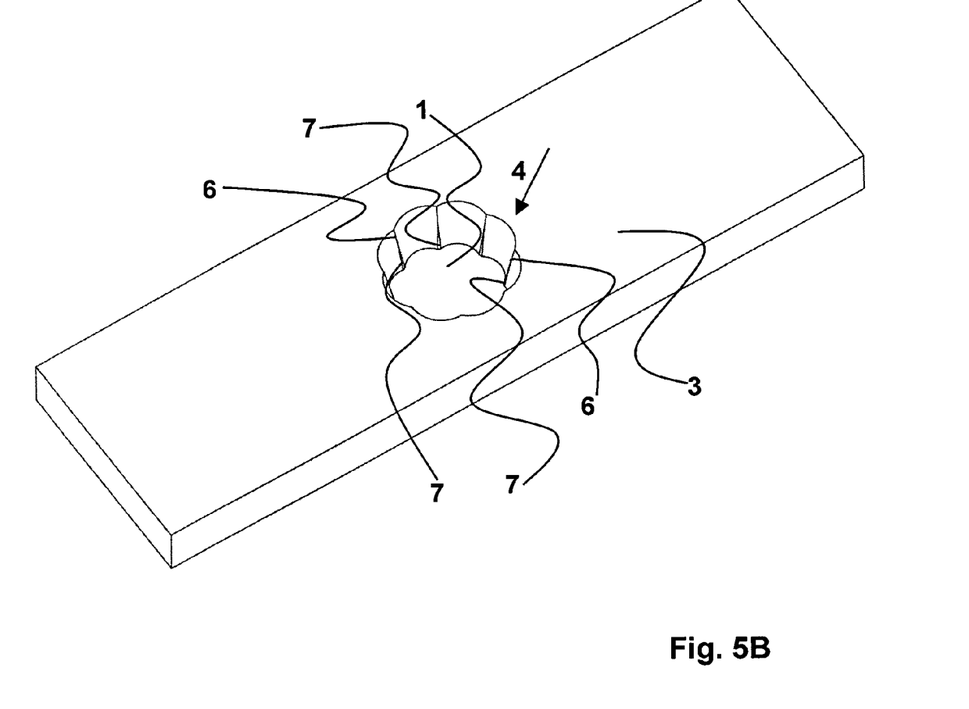
FIG. 5B shows a perspective view of the plate without screws according to FIG. 5A.
Figure 6:
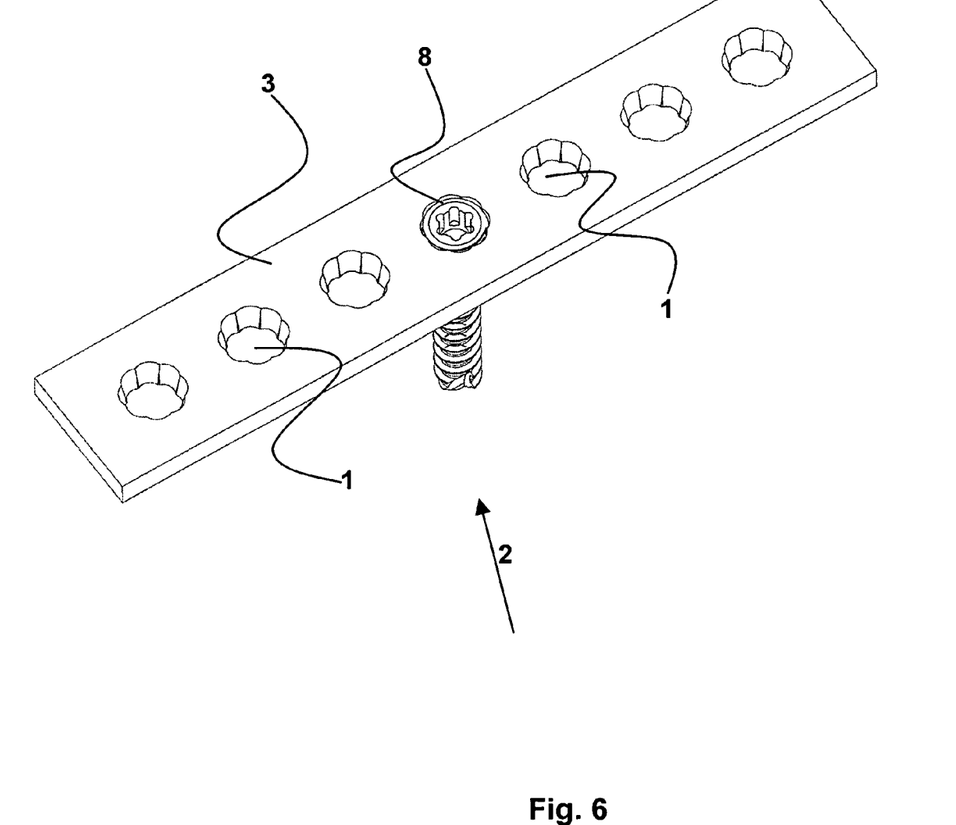
FIG. 6 shows a perspective view of a plate with a multiplicity of through-openings, one through-opening being provided with a screw.
Figure 7:
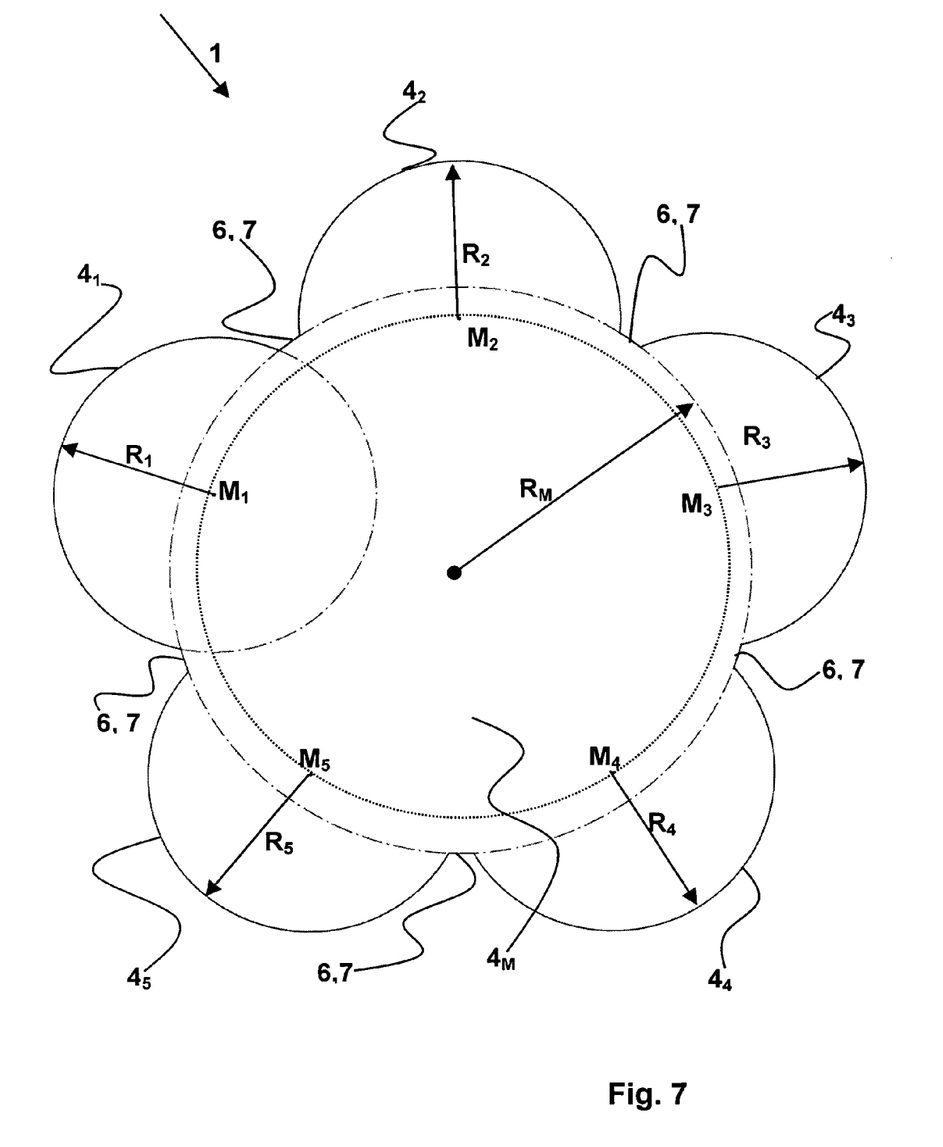
FIG. 7 shows a schematic representation of a through-opening located in a plate and consisting of several cylindrical through-bores, to explain the production.

FIG. 7 is a schematic representation of how a through-opening 1, as shown in FIG. 5B and FIG. 6, is constructed. First, the midpoint M of the through-opening 1 is determined. A radius RM is then determined. This serves to ensure that all the other midpoints $M_1$, $M_2$, $M_3$, $M_4$, $M_5$ lying on the circle with the radius RM are at the same distance from the midpoint $R_M$. The circle with the midpoint $R_M$ is then divided up in such a way that any desired number of other midpoints for other circles are arranged at the same distance from one another. Here in FIG. 6, the circle is divided up in such a way that the midpoints $M_1$, $M_2$, $M_3$, $M_4$, $M_5$ are at the same distance from one another.

A central bore $4_M$ with midpoint M and radius $R_M$ is first to be generated. The central bore 4M, in the illustrative embodiment shown, is cylindrical and uniform through the whole thickness of the plate 3. The first through-bore $4_1$ with a midpoint $M_1$ and a radius $R_1$ is then generated. As soon as the bore is formed, a cylindrical through-bore $4_1$ is obtained. At the points $M_2$ to $M_5$, a through-bore $4_2 \ldots 4_5$ is then formed, specifically with radii $R_2 \ldots R_5$, where the radii $R_1 \ldots R_5$ are identical. This gives rise to the cloverleaf shape with the respective intersection lines 6, which interact with the screw head 9. This embodiment affords the possibility, after production of a central bore 4M, of providing a multiplicity of through-bores $4_x$ with radius $R_x$ and midpoint $M_x$. Here, x is an element of the natural numbers from 1 to infinity.

Figure 8:
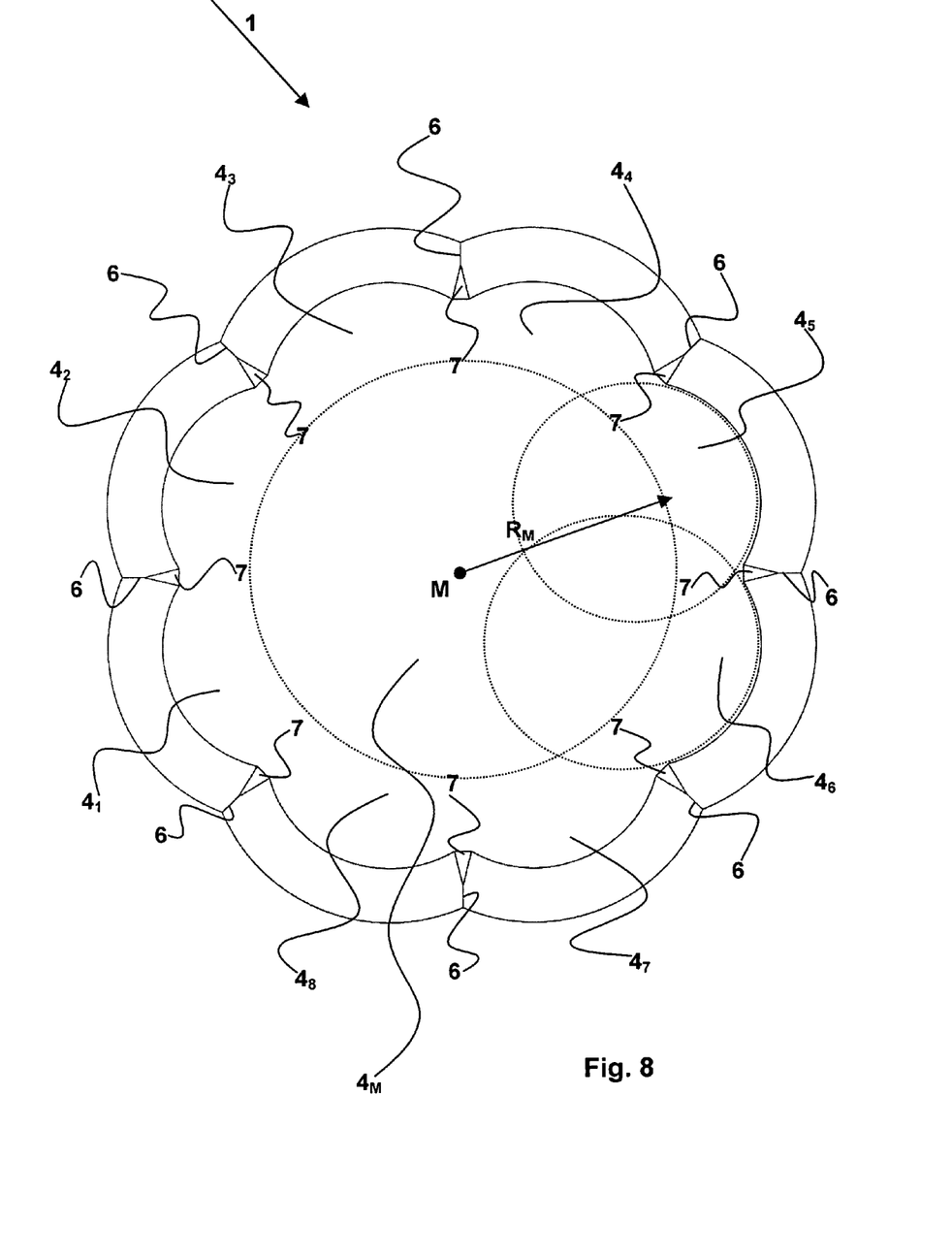
FIG. 8 shows another schematic representation of a through-opening located in a plate and consisting of several conical through-bores.

FIG. 8 shows another embodiment of the configuration according to FIG. 7. First, a central bore 4M with midpoint M and radius $R_M$ is to be generated. The central bore $4_M$, in the illustrative embodiment shown, is conical in shape and narrows through the thickness of the plate 3, starting from the top face of the plate. The defined conicity, that is to say a change of the diameter of the cone as a function of the thickness of the plate, is chosen such that the diameter narrows in the screwing direction of the screw. By virtue of the fact that the other through-bores fully intersect the central bore $4_M$, it suffices for the central bore $4_M$ to be designed cylindrically.

The first through-bore $4_1$ with a midpoint $M_1$ and a radius $R_1$ is then generated. The through-bore $4_1$, in the illustrative embodiment shown, is conical in shape and narrows through the thickness of the plate 3. As soon as the bore is formed, a conical through-bore $4_1$ is obtained. At the points $M_2$ to $M_5$, a through-bore $4_2 \ldots 4_5$ is then once again formed, specifically with radii $R_2 \ldots R_5$, where the radii $R_1 \ldots R_5$ and the conicities are identical. This gives rise, in a plan view, to the cloverleaf shape with the respective intersection lines 6, which interact with the screw head 9. Additional intersection surfaces 7 are additionally obtained on account of the conicities of the through-bores, preferably in continuation of the intersection line 6. This means that the intersection lines 6 merge with increasing depth into intersection surfaces 7. In FIG. 8 is shown the upper radius $R_{60}$ of the through-bore $4_6$ with the midpoint $M_6$. The lower radius $R_{6u}$ is also shown. A milling-cutter is using for producing the mentioned through-bores $4_x$. This milling-cutter shows these to radii $R_{xu}$ and $R_{xo}$. The radii $R_{50}$, $R_{5u}$, $R_{60}$, $R_{6u}$ are only shown for illustrating the manufacturing of the though-opening 1. Radii $R_{xu}$, $R_{x0}$ as well the midpoints $M_x$ have to be transformed to each through-bore $4_x$.

After using said milling-cutter for making the through-bores $4_x$ seen from the top the intersection lines 6, the intersection surfaces 7 and the surfaces F on the top of the plate are formed. In the illustrative embodiments shown in FIGS. 5B and 8, the intersection surfaces 7 are on that side of the plate 3 facing toward the bone and occupy about ⅓ of the depth of the plate.

The number of through-bores can be chosen freely. It has been found that a multiplicity of through-bores reduces the screwing-in force of the screw. The more through-bores there are, the greater the number of intersection surfaces and intersection lines. However, the present thickness (seen from the plan view) of the intersection lines and surfaces is smaller.

Figure 9:
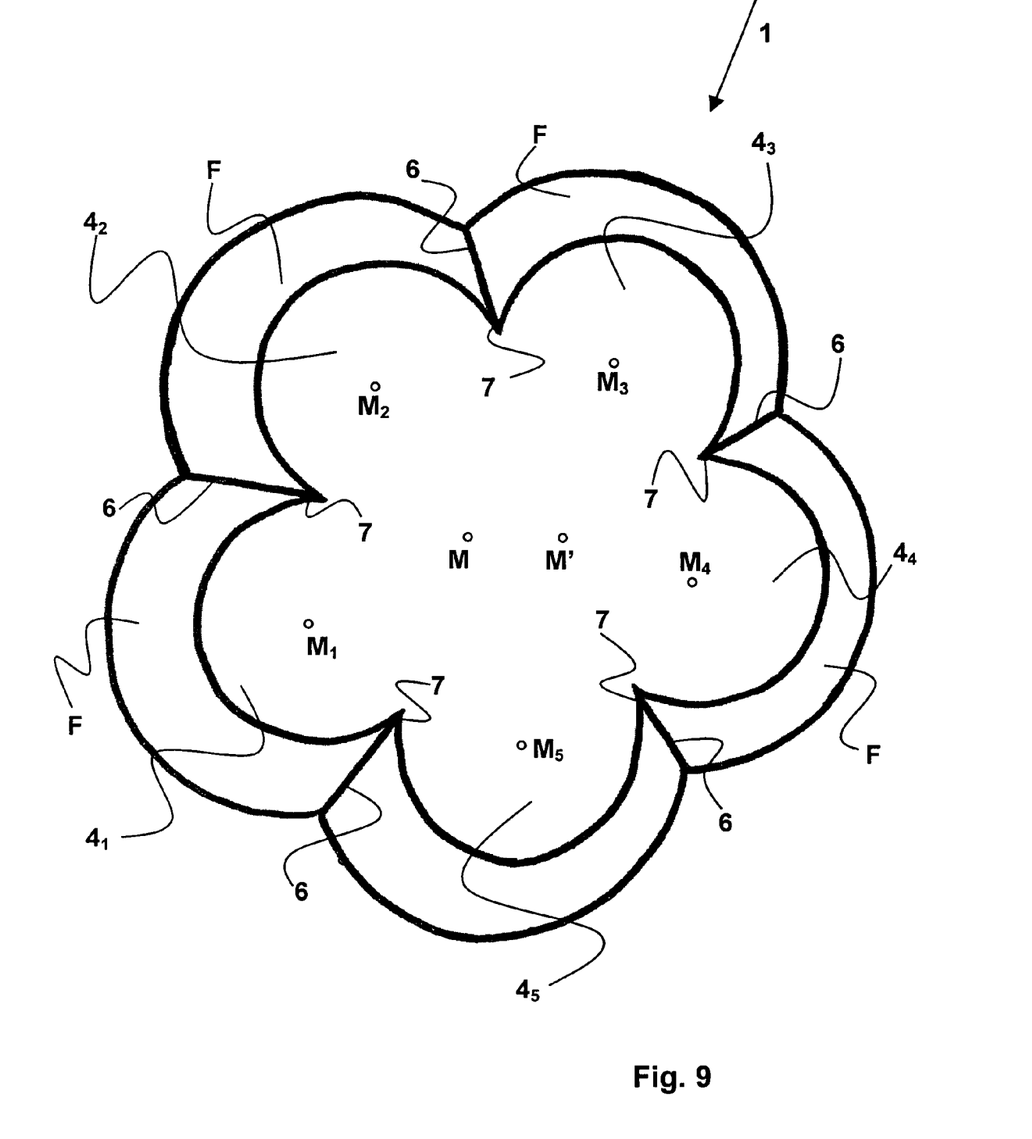
FIG. 9 shows another schematic representation of another illustrative embodiment of a through-opening located in a plate and consisting of several conical through-bores.

In contrast to FIG. 8, more through-bores are provided, and the through-bores $4_1 \ldots 4_8$ are conical, these through-bores narrowing toward the bone K.

FIG. 9 shows another embodiment where the conical surfaces, in contrast to FIG. 8, are of asymmetrical design. The asymmetry is obtained by providing two central through-bores, each with a midpoint M, M'. Starting from these respective midpoints, there extend in different distance the respective midpoint $M_x$ ($M_1 \ldots M_5$) in different length or different distance. This gives rise, in plan view, to a rosette-shaped configuration of the through-opening 1 according to the invention, a slightly offset rosette formation which forms oblique bearing faces F of different length. The intersection lines 6 seen in plan view then merge, as also in the previous examples, with increasing depth into intersection surfaces.

FIGS. 5A to 9 in particular show embodiments of the through-opening according to the invention of special configuration. As a result of the conical design of the respective through-opening, an intersection line is first obtained in the screwing direction which, with increasing depth in the direction of the bone, forms an intersection surface. This can be clearly seen from FIG. 5B in particular. This affords the advantage that only a few thread windings initially interact with the intersection line during screwing-in and exert there a slight plastic deformation, and the deeper the screw is screwed in the greater the interaction between the intersection line or intersection surface and the thread of the respective screw has to be. This has the result that, because of the plastic deformation, a connection is obtained that is almost non-releasable.

As an alternative to this conical design, provision is also made that the through-bores arranged around the central bore are each arranged at an angle, such that the through-opening also narrows toward the bottom. In this way, it is not necessary to produce conical bores exclusively. It is therefore also possible, after the central bore has been produced, to provide such configurations as are shown in FIGS. 5 to 9. By the oblique arrangement of the respective drills for producing the through-bore with respective midpoint $M_x$ and radius $R_x$, where x is an element of the natural numbers 1 to infinity, it is therefore possible that a self-locking screw fastener system formed of screw and plate be used in the orthopedic sector.

The orthopedic screw fastener system thus represents an important innovation over the prior art, since it consists exclusively of two elements, but has properties hitherto known only with several elements in a complex construction. As a result of the cloverleaf-shaped structure of the through-opening, the screw can be screwed in at different angles. The system is distinguished by the fact that the screw is secured against undesired loosening.

LIST OF REFERENCE SIGNS 1 through-opening
2 orthopedic fixation system/screw fastener system
3 plate
4 through-bores
$4_x$ through-bores
5 distance
6 intersection lines
7 intersection surfaces
8 screw
9 screw head
10 screw shank
11 thread
12 thread
13 bore
14 underside of plate
$R_x$ radius
$M_x$ midpoint
K bone
F surface

The invention claimed is:
1. An orthopedic screw fastener system, comprising:
a screw; and
a plate-like main element comprising:
at least one through opening, each through opening comprising:
  a central opening having a central radius and a central midpoint; and
  five radial through bores spaced around said central opening, said five radial through bores comprising:
    a first radial through bore having a first radius and a first midpoint;
    a second radial through bore having a second radius and a second midpoint;
    a third radial through bore having a third radius and a third midpoint;
    a fourth radial through bore having a fourth radius and a fourth midpoint; and
    a fifth radial through bore having a fifth radius and a fifth midpoint;
  five intersection surfaces, comprising:
    a first intersection surface formed from a common intersection of said central opening with said first radial through bore and said second radial through bore;
    a second intersection surface formed from a common intersection of said central opening with said second radial through bore and said third radial through bore;
    a third intersection surface formed from a common intersection of said central opening with said third radial through bore and said fourth radial through bore;

a fourth intersection surface formed from a common intersection of said central opening with said fourth radial through bore and said fifth radial through bore; and a fifth intersection surface formed from a common intersection of said central opening with said fifth radial through bore and said first radial through bore;

five intersection lines comprising:

a first intersection line formed from a common intersection of said first radial through bore and said second radial through bore;

a second intersection line formed from a common intersection of said second radial through bore and said third radial through bore;

a third intersection line formed from a common intersection of said third radial through bore and said fourth radial through bore;

a fourth intersection line formed from a common intersection of said fourth radial through bore and said fifth radial through bore; and a fifth intersection line formed from a common intersection of said fifth radial through bore and said first radial through bore.

2. The orthopedic screw fastener system as in claim 1, wherein each midpoint of said five through bores is disposed within said central radius of said central opening.

3. The orthopedic screw fastener system as in claim 1, wherein said five intersection surfaces are unthreaded throughout an entire length of said intersection surfaces.

4. An orthopedic screw fastener system, comprising:

at least one screw, comprising in each case a screw head and a screw shank, the screw head having a thread, and at least one plate, each comprising:

a through opening comprising:

a central opening with a central midpoint M, and a central radius RM starting at said central midpoint M; and a plurality of radial bores comprising:

at least five radial bores each comprising a radius R starting on a common arc of a circle around the central midpoint M and wherein a midpoint of at least one radial bore of said at least five radial bores is arranged at a same distance to the central midpoint M as an adjacent midpoint of an adjacent radial bore of said at least five radial bores;

wherein said through opening is configured to receive one of said at least one screw, said through opening further comprising:

a plurality of intersecting lines formed in said through opening of said at least one plate, wherein said plurality of intersecting lines are formed by common intersections of each pair of adjacent radial bores of said at least five radial bores and wherein said plurality of intersection lines extend from a top side of said at least one plate to a bottom side of said at least one plate so that said at least one screw interacts with at least one of said plurality of intersecting lines when screwed into said at least one plate; and a plurality of intersection surfaces comprising at least five intersection surfaces comprising:

a first intersection surface formed from an intersection of a first radial bore and a second radial bore of said at least five radial bores and said central opening;

a second intersection surface formed from an intersection of said second radial bore and a third radial bore of said at least five radial bores and said central opening;

a third intersection surface formed from an intersection of said third radial bore and a fourth radial bore of said at least five radial bores and said central opening;

a fourth intersection surface formed from an intersection of said fourth radial bore and a fifth radial bore of said at least five radial bores and said central opening; and a fifth intersection surface.

5. The orthopedic screw fastener system as claimed in claim 4, wherein said plurality of intersecting lines extend in a longitudinal direction of said plurality of radial bores, and wherein said plurality of radial bores are cylindrical.

6. The orthopedic screw fastener system as claimed in claim 4, wherein said through opening is substantially conical in shape.

7. The orthopedic screw fastener system as claimed in claim 4, wherein, in a screwing-in direction of the through opening, each intersection surface of said at least five intersection surfaces provides for greater interaction with said thread of said screw head of said at least one screw than a corresponding one of said plurality of intersection lines.

8. The orthopedic screw fastener system as in claim 4, wherein for each radial bore, its midpoint is spaced at a same distance from midpoints of two adjacent radial bores.

* * * * *